(12) United States Patent
Perera et al.

(10) Patent No.: US 11,280,732 B2
(45) Date of Patent: Mar. 22, 2022

(54) DETECTION OF MELANOMA AND LYMPHOMA BY ATR-FTIR SPECTROSCOPY

(71) Applicant: GEORGIA STATE UNIVERSITY RESEARCH FOUNDATION, INC., Atlanta, GA (US)

(72) Inventors: A. G. Unil Perera, Mableton, GA (US); Hemendra Mani Ghimire, Decatur, GA (US)

(73) Assignee: GEORGIA STATE UNIVERSITY RESEARCH FOUNDATION, INC., Atlanta, GA (US)

(*) Notice: Subject to any disclaimer, the term of this patent is extended or adjusted under 35 U.S.C. 154(b) by 332 days.

(21) Appl. No.: 16/545,409

(22) Filed: Aug. 20, 2019

(65) Prior Publication Data

US 2020/0056991 A1 Feb. 20, 2020

Related U.S. Application Data

(60) Provisional application No. 62/719,755, filed on Aug. 20, 2018.

(51) Int. Cl.
*G01N 21/00* (2006.01)
*G01N 21/552* (2014.01)
*G01N 21/35* (2014.01)
*A61B 5/00* (2006.01)

(52) U.S. Cl.
CPC ........ *G01N 21/552* (2013.01); *A61B 5/0059* (2013.01); *A61B 5/444* (2013.01); *A61B 5/7257* (2013.01); *G01N 21/35* (2013.01); *G01N 2021/3595* (2013.01)

(58) Field of Classification Search
CPC .......... G01N 15/0205; G01N 15/1459; G01N 21/29; G01N 2015/1486; G01N 21/53
USPC ....................................................... 356/337
See application file for complete search history.

(56) References Cited

U.S. PATENT DOCUMENTS

| | | | |
|---|---|---|---|
| 3,393,603 | A | 7/1968 | Harrick |
| 4,602,869 | A | 7/1986 | Harrick |
| 6,146,897 | A | 11/2000 | Cohenford et al. |
| 6,395,538 | B1 | 5/2002 | Naughton |
| 7,524,681 | B2 | 4/2009 | Wolf et al. |
| 8,614,419 | B2 | 12/2013 | Buffington et al. |

(Continued)

FOREIGN PATENT DOCUMENTS

| | | |
|---|---|---|
| WO | 9517092 | 6/1995 |
| WO | 2009121054 | 10/2009 |

(Continued)

OTHER PUBLICATIONS

Ahmad, M., et al., "Butyrate and glucose metabolism by colonocytes in experimental colitis in mice" Gut, 2000. 46(4):493-499.

(Continued)

*Primary Examiner* — Md M Rahman
(74) *Attorney, Agent, or Firm* — Meunier Carlin & Curfman LLC (57) ABSTRACT

The present disclosure relates to methods for the detection of melanoma and non-Hodgkin's lymphoma using attenuated total reflection Fourier transform infrared (ATR-FTIR) spectroscopy. Further disclosed are methods for treating melanoma and non-Hodgkin's lymphoma, based on differences in infrared absorbance.

20 Claims, 3 Drawing Sheets

(56) References Cited

U.S. PATENT DOCUMENTS

| | | |
|---|---|---|
| 2004/0121491 A1 | 6/2004 | Marchand-Brynaert |
| 2004/0133086 A1 | 7/2004 | Ciurczak et al. |
| 2010/0130868 A1 | 5/2010 | Hargrove et al. |
| 2011/0059023 A1 | 3/2011 | Tunnell et al. |
| 2012/0225474 A1 | 9/2012 | Wagner et al. |
| 2016/0305877 A1 | 5/2016 | Titus et al. |

FOREIGN PATENT DOCUMENTS

| | | |
|---|---|---|
| WO | 2014076480 | 5/2014 |
| WO | 2015085056 | 6/2015 |

OTHER PUBLICATIONS

Amaria, R. N., et al., "Update on use of aldesleukin for 30 treatment of high-risk metastatic melanoma," ImmunoTargets and therapy, vol. 4, p. 79, 2015.

Andrus, Paul GL, et al., "Cancer grading by Fourier transform infrared spectroscopy." Biospectroscopy 4.1 (1998): 37-46.

Argov, Shmuel, et al. "Inflamatory bowel diseases as an intermediate stage between normal and cancer: A FTIR-microspectroscopy approach." Biopolymers: Original Research on Biomolecules 75.5 (2004): 384-392.

Ariyawansa, G., et al., "Multi-colored tunneling quantum dot infrared photodetectors operating at room temperature" Infrared Physics & Technology, 2007.50(2-3):156-161.

Backhaus, Juergen, et al. "Diagnosis of breast cancer with infrared spectroscopy from serum samples." Vibrational Spectroscopy 52.2 (2010): 173-177.

Baker, Matthew J., et al. "Developing and understanding biofluid vibrational spectroscopy: a critical review." Chemical Society Reviews 45.7 (2016): 1803-1818.

Baker, Matthew J., et al. "Using Fourier transform IR spectroscopy to analyze biological materials." Nature protocols 9.8 (2014): 1771.

Barth, Andreas. "Infrared spectroscopy of proteins." Biochimica et Biophysica Acta (BBA)-Bioenergetics 1767.9 (2007): 1073-1101.

Bellisola, Giuseppe, and Claudio Sorio. "Infrared spectroscopy and microscopy in cancer research and diagnosis." American journal of cancer research 2.1 (2012): 1.

Bian, Z., et al., "Cd47-Sirp α interaction and IL-10 constrain inflammation-induced macrophage phagocytosis of healthy self-cells," Proceedings of the National Academy of Sciences, vol. 113, pp. E5434-E5443, 2016.

Bogomolny, E., Huleihel, M., Suproun, Y., Sahu, R. K. & Mordechai, S. "Early spectral changes of cellular malignant transformation using Fourier transform infrared microspectroscopy." Journal of biomedical optics 12, 024003-024003-024009 (2007).

Byler, D. M. & Susi, H. "Examination of the secondary structure of proteins by deconvolved FTIR spectra." Biopolymers 25, 469-487 (1986).

Chan, K. A. & Kazarian, S. G. "Attenuated total reflection Fourier-transform infrared (ATR-FTIR) imaging of tissues and live cells." Chemical Society Reviews 45, 1850-1864 (2016).

Chassaing, B., et al., "Dextran sulfate sodium (DSS)-induced colitis in mice" Current Protocols in Immunology. John Wiley & Sons, Inc, Hoboken, NJ; 2014 (15.25.1-15.25.14).

Chassaing, B., et al., "Fecal Lipocalin 2, a Sensitive and Broadly Dynamic Non-Invasive Biomarker for Intestinal Inflammation" PloS one, 2012. 7(9):e44328.

Cheadle, Chris, et al. "Control of gene expression during T cell activation: alternate regulation of mRNA transcription and mRNA stability." BMC genomics 6.1 (2005): 75.

Chirgadze, Y. N. & Nevskaya, N. "Infrared spectra and resonance interaction of amide-I vibration of the antiparallel-chain pleated sheet." Biopolymers 15, 607-625 (1976).

Clapper, M.L., et al., "Dextran sulfate sodium-induced colitis-associated neoplasia: a promising model for the development of chemopreventive interventions" Acta pharmacologica Sinica, 2007. 28(9): 1450-1459.

Crabtree, Gerald R. "Contingent genetic regulatory events in T lymphocyte activation." Science 243.4889 (1989): 355-361.

Daydé, D et al. "Tumor burden influences exposure and response to rituximab: pharmacokinetic-pharmacodynamic modeling using a syngeneic bioluminescent murine model expressing human CD20." Blood 113, 3765-3772 (2009).

Erukhimovitch, V., et al. "Infrared spectral changes identified during different stages of herpes viruses infection in vitro." Analyst 136.13 (2011): 2818-2824.

Erukhimovitch, Vitaly, et al. "FTIR microscopy detection of cells infected with viruses." DNA Viruses. Humana Press, 2005. 161-172.

Extended European Search Report, issued for European Application No. 16808503.3, dated Dec. 3, 2018.

Fisher, R. I., et al., "Comparison of a standard regimen (CHOP) with three intensive chemotherapy regimens for advanced non-Hodgkin's lymphoma," New England Journal of Medicine, vol. 328, pp. 1002-1006, 1993.

Fisher, S. G. & Fisher, R. I. "The epidemiology of non-Hodgkin's lymphoma." Oncogene 23, 6524-6534 (2004).

Friedman, S, et al. "Screening and Surveillance Colonoscopy in Chronic Crohn's Colitis" Gastroenterology. 2001 120(4):820-6.

Fujioka, N., Morimoto, Y., Arai, T. & Kikuchi, M. "Discrimination between normal and malignant human gastric tissues by Fourier transform infrared spectroscopy." Cancer Detection and Prevention 28, 32-36 (2004).

Gajjar, K. et al. "Diagnostic segregation of human brain tumours using Fourier-transform infrared and/or Raman spectroscopy coupled with discriminant analysis." Analytical Methods 5, 89-102 (2013).

Garbe, C. & Leiter, U. "Melanoma epidemiology and trends." Clinics in dermatology 27, 3-9 (2009).

Gazi, E. et al. "A correlation of FTIR spectra derived from prostate cancer biopsies with Gleason grade and tumour stage." European urology 50, 750-761 (2006).

Gazi, E. et al. "Applications of Fourier transform infrared micro spectroscopy in studies of benign prostate and prostate cancer. A pilot study." The Journal of pathology 201, 99-108 (2003).

Goormaghtigh, Erik, Véronique Cabiaux, and Jean-Marie Ruysschaert. "Determination of soluble and membrane protein structure by Fourier transform infrared spectroscopy." Physicochemical methods in the study of biomembranes. Springer, Boston, MA, 1994. 405-450.

Hammody, Z., Sahu, R. K., Mordechai, S., Cagnano, E. & Argov, S. "Characterization of malignant melanoma using vibrational spectroscopy." The Scientific World Journal 5, 173-182 (2005).

Hands, J. R. et al. "Attenuated total reflection Fourier transform infrared (ATR-FTIR) spectral discrimination of brain tumour severity from serum samples." J. Biophotonics 7, 189-199 (2014).

Hands, J. R. et al. "Brain tumour differentiation: rapid stratified serum diagnostics via attenuated total reflection Fourier-transform infrared spectroscopy." Journal of neurooncology 127, 463-472 (2016).

Hastings, Gary, et al. "Viral infection of cells in culture detected using infrared microscopy." Analyst 134.7 (2009): 1462-1471.

Hilliard, Julia, et al. Cell Biosensors: Rapid Detection and Identification of Pathogens Using FTIR Microspectroscopic Spectra. No. RTO-MP-HFM-182. Georgia State Univ Atlanta Dept of Biology, 2010.

Howlader, N. et al. "Contributions of Subtypes of Non-Hodgkin Lymphoma to Mortality Trends", Cancer Epidemiol Biomarkers Prev. Jan. 2016; 25(1): 174-179.

International Search Report and Written Opinion issued in related International Application No. PCT/US2016/037172 dated Sep. 1, 2016.

International Search Report and Written Opinion, issued in International Application No. PCT/US14/68542, dated Apr. 7, 2015.

Jayaweera, P. et al. "Uncooled infrared detectors for 3-5 μ m and beyond". Applied Physics Letters 93, 021105 (2008).

Jayaweera, P.V.V., et al., "Displacement currents in semiconductor quantum dots embedded dielectric media: A method for room temperature photon detection" Applied Physics Letters, 2007. 91(6):063114.

(56) References Cited

OTHER PUBLICATIONS

Jerant, A. F., Johnson, J. T., Sheridan, C. & Caffrey, T. J. "Early detection and treatment of skin cancer." American family physician 62, 357-386 (2000).
Kazarian, S. G. & Chan, K. A. "ATR-FTIR spectroscopic imaging: recent advances and applications to biological systems." Analyst 138, 1940-1951 (2013).
Kennedy, R., et al., "Interleukin 10-deficient colitis: new similarities to human inflammatory bowel disease" British journal of surgery, 2000. 87(10):1346-1351.
Kim, J.J., et al., "Investigating Intestinal Inflammation in DSS-induced Model of IBP" Journal of Visualized Experiments: JoVE, 2012(60):3678.
Kong, J. & Yu, S. "Fourier transform infrared spectroscopic analysis of protein secondary structures." Acta biochimica et biophysica Sinica 39, 549-559 (2007).
Kombluth A, et al.: "How effective is current medical therapy for severe ulcerative and Crohn's colitis? An analytic review of selected trials." J Clin Gastroenterol. 1995 20(4):280-4.
Laroui, H., et al., "Dextran Sodium Sulfate (DSS) Induces Colitis in Mice by Forming Nano-Lipocomplexes with Medium-Chain-Length Fatty Acids in the Colon" PloS one, 2012. 7(3):e32084.
Lee-Montiel, K. A. Reynolds and M. R. Riley, Journal of biological engineering 5, 16 (2011).
Legouffe, E. et al. "C-reactive protein serum level is a valuable and simple prognostic marker in non Hodgkin's lymphoma." Leukemia & lymphoma 31, 351-357 (1998).
Lens, M. & Dawes, M. "Global perspectives of contemporary epidemiological trends of cutaneous malignant melanoma." British Journal of Dermatology 150, 179-185 (2004).
Lens, M. & Newton-Bishop, J. "An association between cutaneous melanoma and non-Hodgkin's lymphoma: pooled analysis of published data with a review." Annals of oncology 16, 460-465 (2005).
Lewis, P. D. et al. "Evaluation of FTIR spectroscopy as a diagnostic tool for lung cancer using sputum." BMC cancer 10, 640 (2010).
Lima, C. A., Goulart, V. P., Côrrea, L., Pereira, T. M. & Zezell, D. M. "ATR-FTIR spectroscopy for the assessment of biochemical changes in skin due to cutaneous squamous cell carcinoma." International journal of molecular sciences 16, 6621-6630 (2015).
Lu, R. et al. "Probing the secondary structure of bovine serum albumin during heatinduced denaturation using mid-infrared fiberoptic sensors." Analyst 140, 765-770 (2015).
Maconi, G., et al., "Glucose intolerance and diabetes mellitus in ulcerative colitis: Pathogenetic and therapeutic implications" World Journal of Gastroenterology: WJG, 2014. 20(13):3507-3515.
Meurens, M., Wallon, J., Tong, J., Noel, H. & Haot, J. "Breast cancer detection by Fourier transform infrared spectrometry." Vibrational spectroscopy 10, 341-346 (1996).
Mordechai, S. et al. "Possible common biomarkers from FTIR microspectroscopy of cervical cancer and melanoma." Journal of microscopy 215, 86-91 (2004).
Movasaghi, Z., et al. "Fourier Transform Infrared (FTIR) Spectroscopy of Biological Tissues" Applied Spectroscopy Reviews, 2008. 43(2):134-179.
Movasaghi, Z., Rehman, S. & ur Rehman, D. I. "Fourier transform infrared (FTIR) spectroscopy of biological tissues." Applied Spectroscopy Reviews 43, 134-179 (2008).
Nykänen, P., "Degradation of thymidine to thymine by rheumatoid arthritis synovial tissue eluate" Scandinavian journal of immunology, 1979. 9(5):477-482.
Ollesch, J. et al. "It's in your blood: spectral biomarker candidates for urinary bladder cancer from automated FTIR spectroscopy." Journal of biophotonics 7, 210-221 (2014).
Orphanou, C.-M. "The detection and discrimination of human body fluids using ATR FTIR spectroscopy." Forensic science international 252, e10-e16 (2015).
Overwijk, W. W. & Restifo, N. P. "B16 as a mouse model for human melanoma." Current Protocols in Immunology, 20.21. 21-20.21. 29 (2001).

Perera, A., et al., "High operating temperature split-off band infrared detectors." Applied Physics Letters, 2006. 89(13):131118.
Perera, A.G.U., et al., "Room temperature nano- and microstructure photon detectors" Microelectronics Journal, 2009. 40(3):507-511.
Perše, M. and A. Cerar, "Dextran sodium sulphate colitis mouse model: Traps and tricks" Journal of biomedicine & biotechnology, 2011. 2012:718617-718617.
Petibois, C., et al., "Determination of Glucose in Dried Serum Samples by Fourier-Transform Infrared Spectroscopy" Clinical chemistry, 1999. 45(9):1530-1535.
Pinkerneil, et al., "Surface-Attached Polyhistidine-Tag Proteins Characterized by FTIR Difference Spectroscopy", ChemPhysChem 2012, 13, 2649-2653.
Rigas, B., Morgello, S., Goldman, I. S. & Wong, P. "Human colorectal cancers display abnormal Fourier-transform infrared spectra." Proceedings of the National Academy of Sciences 87, 8140-8144 (1990).
Schicho, R., et al., "Quantitative Metabolomic Profiling of Serum and Urine in DSS-induced Ulcertive Colitis of Mice by 1H NMR Spectroscopy" Journal of Proteome Research, 2010. 9(12):6265-6273.
Schreyer, A, et al., "Comparison of magnetic resonance imaging colonography with conventional colonoscopy for the assessment of intestinal inflammation in patients with inflammatory bowel disease: a feasible study" Gut. 2005 54(2):250-6.
Shipp, M. et al. "A predictive model for aggressive non-Hodgkin's lymphoma." New England Journal of Medicine 329, 987-994 (1993).
Siegel, R. L., Miller, K. D. & Jemal, A. "Cancer statistics, 2016." CA: a cancer journal for clinicians 66, 7-30 (2016).
Sommer, A. J., Tisinger, L. G., Marcott, C. & Story, G. M. "Attenuated total internal reflection infrared mapping microspectroscopy using an imaging microscope." Appl. Spectrosc. 55, 252-256 (2001).
Surewicz, W. K., Mantsch, H. H. & Chapman, D. "Determination of protein secondary structure by Fourier transform infrared spectroscopy: a critical assessment." Biochemistry 32, 389-394 (1993).
Teague, R., et al. "Changes in Monosaccharide Content of Mucous Glycoproteins in Ulcerative Colitis" BMJ, 1973. 2(5867):645-646.
Theophilou, G., Lima, K. M., Martin-Hirsch, P. L., Stringfellow, H. F. & Martin, F. L. "ATR-FTIR spectroscopy coupled with chemometric analysis discriminates normal, borderline and malignant ovarian tissue: classifying subtypes of human cancer." Analyst 141, 585-594 (2016).
Titus, J., Filfili, C., Hilliard, J. K., Ward, J. A. & Unil Perera, A. "Early detection of cell activation events by means of attenuated total reflection Fourier transform infrared spectroscopy." Applied Physics Letters 104, 243705 (2014).
Titus, J., Ghimire, H., Viennois, E., Merlin, D. & Perera, A. Protein secondary structure analysis of dried blood serum using infrared spectroscopy to identify markers for colitis screening. Journal of Biophotonics (2018).
Titus, J., Viennois, E., Merlin, D. & Unil Perera, A. "Minimally invasive screening for colitis using attenuated total internal reflectance fourier transform infrared spectroscopy." Journal of biophotonics 1-8, (2016).
Uemera T. et al.: "Non-Invasive Blood Glucose Measurement by Fourier Transform Infrared Spectroscopic Analysis Through the Mucous Membrane of the Lip: Application of a Chalcogenide Optical Fiber System," Frontiers of Medical and Biological Engineer, VLP. Zeist, NL, vol. 9, No. 2, 1999 (1999), pp. 137, 153.
Ugurel, S., et al., "Dacarbazine in melanoma: from a chemotherapeutic drug to an immunomodulating agent," Journal of Investigative Dermatology, vol. 133, pp. 289-292, 2013.
Vereecken, P., Cornelis, F., Van Baren, N., Vandersleyen, V. & Baurain, J.-F. "A synopsis of serum biomarkers in cutaneous melanoma patients." Dermatology research and practice 2012 (2012).
Viennois, E. et al., "Longitudinal study of circulating protein biomarkers in inflammatory bowel disease" Journal of proteomics 2015, 112:166-179.
Viennois, E., et al., "Micheliolide, a new sesquiterpene lactone that inhibits intestinal inflammation and colitis-associated cancer" Laboratory Investigation, 2014. 94(9):950-965.

(56) References Cited

OTHER PUBLICATIONS

Vijay-Kumar, M., et al., "Metabolic Syndrome and Altered Gut Microbiota in Mice Lacking Toll-Like Receptor 5" Science, 2010. 328(5975):228-231.

Wood, B. et al. "Fourier transform infrared (FTIR) spectral mapping of the cervical transformation zone, and dysplastic squamous epithelium." Gynecologic oncology 93, 59-68 (2004).

Xiang Li et al., "Identification of Colitis and Cancer In Colon Biopsies by Fourier Transform Infrared Spectroscopy and Chemometrics," The Scientific World Journal, vol. 2012, pp. 1-4.

Yang, H., Yang, S., Kong, J., Dong, A. & Yu, S. "Obtaining information about protein secondary structures in aqueous solution using Fourier transform IR spectroscopy." Nature protocols 10, 382-396 (2015).

Yu, C. and J. Irudayaraj, "Spectroscopic Characterization of Microorganisms by Fourier Transform Infrared Microspectroscopy" Biopolymers, 2005. 77(6):368-377.

DETECTION OF MELANOMA AND LYMPHOMA BY ATR-FTIR SPECTROSCOPY

CROSS REFERENCE TO RELATED APPLICATIONS

This application claims the benefit of U.S. Provisional Patent Application Ser. No. 62/719,755 filed August 20, 2018, which is expressly incorporated herein by reference.

STATEMENT REGARDING FEDERALLY SPONSORED RESEARCH

This invention was made with Government Support under Grant No. R01 AI106839 awarded by the National Institutes of Health, Grant No. W911 NF-15-1-0018 awarded by the U.S. Army Research Office, and Grant No. 55655-EL-DURIP awarded by the Air Force Office of Scientific Research. The Government has certain rights in the invention.

FIELD

The present disclosure relates to methods for the detection of melanoma and non-Hodgkin's lymphoma using attenuated total reflection Fourier transform infrared (ATR-FTIR) spectroscopy. Further disclosed are methods for treating melanoma and non-Hodgkin's lymphoma, based on differences in infrared absorbance.

BACKGROUND

The incidence rates of cutaneous melanoma, a deadly form of skin cancer, has been increasing in many regions and populations over the last few decades. The increase has been of the order of 3-7% per year among fair-skinned populations. At the same time, non-Hodgkin's lymphoma (NHL), a solid tumorous condition of the immune system with a wide range of histological appearance and clinical features, accounts for 4.3% of all new cancer cases in the US. Although significant improvement has been made to stabilize the number of NHL cases and to increase its five-year survival rate, the existing diagnostic techniques, which include histological examination using biopsy, are time-consuming, invasive, costly, and are not accessible to the entire at-risk population. Developing a rapid and reliable prescreening strategy for melanoma and lymphoma is thus critical because the early diagnosis and treatment of these malignancies improves the patient's chances of survival.

Fourier Transform Infrared (FTIR) spectroscopy is an attractive technique for a rapid, reliable and affordable screening of multiple diseases. This technique extracts a snapshot of molecular components within the diagnostic medium and provides a holistic biochemistry of that medium. FTIR spectroscopy combined with appropriate data handling frameworks has been applied in oncological studies such as studies involving the cancers of the cervix, the lung, the breast, the skin, the gastro-intestine, the prostate, the colon, the ovary, the urinary bladder, and many other body parts. These studies have reported that the molecular structural rearrangement associated with cancer development alters the vibrational mode of the molecular functional groups of the affected tissues as manifested in spectral markers or signatures. Furthermore, the Attenuated Total Reflection (ATR) sampling mode of FTIR spectroscopy represents a complementary approach for the clinical application, compared to other infrared approaches. In this mode, high-quality results with better spectral reproducibility compared to other modes can be obtained by the use of fluid samples. It has been noted that metabolic discharges into the body fluids (saliva, excreta, blood and other tissue fluids) from the proximate cancerous tissue change the constituent molecules, providing strong guidance for subsequent clinical assessment. ATR-FTIR spectroscopy of body fluids has thus attracted much attention in the scientific community including clinicians for rapid detection of various health conditions. What is needed are improved methods for the detection and treatment of melanoma and non-Hodgkin's lymphoma.

The methods disclosed herein address these and other needs.

SUMMARY

Disclosed herein are novel non-invasive methods for the detection and treatment of melanoma and non-Hodgkin's lymphoma. The inventors have used attenuated total reflection Fourier transform infrared (ATR-FTIR) spectroscopy to assess biochemical changes induced by melanoma or non-Hodgkin's lymphoma. Infrared absorbance values of the different spectral bands, hierarchical clustering and integral values of the component bands by curve fitting, show statistically significant differences between spectra representing healthy and tumorous tissue. Thus, further disclosed are methods for having individualized route maps for rapid evaluation of cancer status (for example, lymphoma and melanoma) and administration of therapeutic treatments.

In one aspect, disclosed herein is a method for detecting melanoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of melanoma;
wherein a difference in absorbance at one or more frequencies compared to the control spectrum is an indication of melanoma in the sample.

In one aspect, disclosed herein is a method for detecting non-Hodgkin's lymphoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of non-Hodgkin's lymphoma;
wherein a difference in absorbance at one or more frequencies compared to the control spectrum is an indication of non-Hodgkin's lymphoma in the sample.

In some embodiments, the IRE comprises a diamond crystal, a germanium crystal, or a zinc selenide crystal. In some embodiments, the IRE comprises a diamond crystal.

In some embodiments, the absorption spectrum is recorded over a range of preselected frequencies. In some embodiments, the range of preselected frequencies is from $50\ cm^{-1}$ to $3700\ cm^{-1}$. In some embodiments, a peak at $1638\text{-}1644\ cm^{-1}$ is an indication of melanoma in the subject. In some embodiments, the method further comprises administering a chemotherapeutic agent if a peak is detected at $1638\text{-}1644\ cm^{-1}$.

In some embodiments, a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is an indication of melanoma in the subject. In some embodiments, the method further comprises administering a chemotherapeutic agent if a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is detected.

In some embodiments, an integral sum for six deconvoluted Gaussian function energy band profiles (from 1000 cm$^{-1}$ to 1140 cm$^{-1}$) of greater than or equal to 14.8 is an indication of melanoma in the subject. In some embodiments, the method further comprises administering a chemotherapeutic agent if an integral sum for six deconvoluted Gaussian function energy band profiles (from 1000 cm$^{-1}$ to 1140 cm$^{-1}$) of greater than or equal to 14.8 is detected.

In some embodiments, the sample is a tissue sample, skin sample, blood sample, serum sample, or plasma sample. In some embodiments, the method further comprises Fourier transformation of the absorbance spectrum.

In some aspects, disclosed herein is a method for treating melanoma, comprising:
detecting melanoma, comprising:
  depositing a sample comprising a plurality of cells on an internal reflection element (IRE);
  directing a beam of infrared (IR) radiation through the IRE under conditions such that the IR radiation interacts with the plurality of cells;
  recording an absorption spectrum; and
  comparing the absorption spectrum to a control spectrum to detect the presence of melanoma; and
administering a chemotherapeutic agent if:
  i) a peak is detected at 1638-1644 cm$^{-1}$; or
  ii) a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is detected; or
  iii) an integral sum for six deconvoluted Gaussian function energy band profiles (from 1000 cm$^{-1}$ to 1140 cm$^{-1}$) of greater than or equal to 14.8 is detected.

In some aspects, disclosed herein is a method for treating non-Hodgkin's lymphoma, comprising:
detecting non-Hodgkin's lymphoma, comprising:
  depositing a sample comprising a plurality of cells on an internal reflection element (IRE);
  directing a beam of infrared (IR) radiation through the IRE under conditions such that the IR radiation interacts with the plurality of cells;
  recording an absorption spectrum; and
  comparing the absorption spectrum to a control spectrum to detect the presence of non-Hodgkin's lymphoma; and
administering a chemotherapeutic agent if:
  i) a peak is detected at 1636-1642 cm$^{-1}$; or
  ii) a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is detected; or
  iii) an integral sum for six deconvoluted Gaussian function energy band profiles (from 1000 cm$^{-1}$ to 1140 cm$^{-1}$) of greater than or equal to 14.8 is detected.

In some embodiments, the IRE comprises a diamond crystal, a germanium crystal, or a zinc selenide crystal. In some embodiments, the IRE comprises a diamond crystal.

In some embodiments, the absorption spectrum is recorded over a range of preselected frequencies. In some embodiments, the range of preselected frequencies is from 50 cm$^{-1}$ to 3700 cm$^{-1}$. In some embodiments, a peak at 1636-1642 cm$^{-1}$ is an indication of non-Hodgkin's lymphoma in the subject. In some embodiments, the method further comprises administering a chemotherapeutic agent if a peak is detected at 1636-1642 cm$^{-1}$.

In some embodiments, a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is an indication of non-Hodgkin's lymphoma in the subject. In some embodiments, the method further comprises administering a chemotherapeutic agent if a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is detected.

In some embodiments, an integral sum for six deconvoluted Gaussian function energy band profiles (from 1000 cm$^{-1}$ to 1140 cm$^{-1}$) of greater than or equal to 14.8 is an indication of non-Hodgkin's lymphoma in the subject. In some embodiments, the method further comprises administering a chemotherapeutic agent if an integral sum for six deconvoluted Gaussian function energy band profiles (from 1000 cm$^{-1}$ to 1140 cm$^{-1}$) of greater than or equal to 14.8 is detected.

In some embodiments, the sample is a tissue sample, skin sample, blood sample, serum sample, or plasma sample. In some embodiments, the method further comprises Fourier transformation of the absorbance spectrum.

BRIEF DESCRIPTION OF THE DRAWINGS

The accompanying figures, which are incorporated in and constitute a part of this specification, illustrate several aspects described below.

FIG. 1. The discriminatory region of infrared absorbance spectra. (a) Average normalized ATR-FTIR spectra of serum samples extracted from EL4-lymphoma (n=8), B16-melanoma (n=8) mouse models in wild types and corresponding control types (n=15). The inset (i) shows B16-melanoma mouse with tumor size approximately 1000 mm$^3$ (day 18). Increase in volume of the tumor from the day 9 to day 18 of tumor inoculation in B16-melanoma mouse is as in inset (ii). Similar to the B16 mouse, elevation of tumor size is also monitored in EL4-lymphoma. The serum sample is extracted for both types of mice when tumor size becomes bigger than 1000 mm$^3$. (b) Student's t-test (two-tailed unequal variance) p-values of absorbance. Discriminatory region for lymphoma with higher significance (p<0.05) are amide I of protein, amide II of protein, C—H bends of CH$_3$/CH$_2$ groups in α- and β-anomers, asymmetric phosphate I, and carbohydrates with predominant contributions nucleic acids (DNA/RNA via PO$_2^-$ stretches). Discriminatory regions of melanoma are amide I and carbohydrates with predominant contributions of nucleic acids.

FIG. 2. Protein secondary structure analysis. (a) The representative of the second derivatives of the ATR-FTIR absorbance spectra confined to amide I band. (b) Deconvolution of amide I region: baseline corrected spectra were fitted with six Gaussian band profiles by approximating number and position using the minima of second derivatives, which simulated fits to the experimental curve. Six Gaussian band profiles are assigned as (1) side chain (~1610 $cm^{-1}$), (2) β sheet (1630 $cm^{-1}$), (3) random coil (~1645 $cm^{-1}$), (4) α helix (~1652 $cm^{-1}$), (5) β turn (~1682 $cm^{-1}$) and (6) β anti-parallel sheet (~1690 $cm^{-1}$) structures. (c) Averaged Gaussian function energy bands of each studied types which prove elevation of β sheet and drop off α helix structures due to malignancies, while other structures remain same.

DETAILED DESCRIPTION

Disclosed herein are novel non-invasive methods for the detection and treatment of melanoma and non-Hodgkin's lymphoma. The inventors have used attenuated total reflection Fourier transform infrared (ATR-FTIR) spectroscopy to assess biochemical changes induced by melanoma or non-Hodgkin's lymphoma. Infrared absorbance values of the different spectral bands, hierarchical clustering and integral values of the component bands by curve fitting, show statistically significant differences between spectra representing healthy and tumorous tissue. Thus, further disclosed are methods for having individualized route maps for rapid evaluation of cancer status (for example, lymphoma and melanoma) and administration of therapeutic treatments.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The term "about" as used herein when referring to a measurable value such as an amount, a percentage, and the like, is meant to encompass variations of ±20%, ±10%, ±5%, or ±1% from the measurable value.

Methods of Detection and Treatment

In one aspect, disclosed herein is a method for detecting melanoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of melanoma;
wherein a difference in absorbance at one or more frequencies compared to the control spectrum is an indication of melanoma in the sample.

In one aspect, disclosed herein is a method for detecting non-Hodgkin's lymphoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of non-Hodgkin's lymphoma;
wherein a difference in absorbance at one or more frequencies compared to the control spectrum is an indication of non-Hodgkin's lymphoma in the sample.

In some embodiments, the IRE comprises a diamond crystal, a germanium crystal, or a zinc selenide crystal. In some embodiments, the IRE comprises a diamond crystal.

In some embodiments, the absorption spectrum is recorded over a range of preselected frequencies. In some embodiments, the range of preselected frequencies is from 50 $cm^{-1}$ to 3700 $cm^{-1}$. In some embodiments, a peak at 1638-1644 $cm^{-1}$ is an indication of melanoma in the subject. In some embodiments, the method further comprises administering a chemotherapeutic agent if a peak is detected at 1638-1644 $cm^{-1}$.

In some embodiments, a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is an indication of melanoma in the subject. In some embodiments, the method further comprises administering a chemotherapeutic agent if a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is detected.

In some embodiments, an integral sum for six deconvoluted Gaussian function energy band profiles (from 1000 $cm^{-1}$ to 1140 $cm^{-1}$) of greater than or equal to 14.8 is an indication of melanoma in the subject. In some embodiments, the method further comprises administering a chemotherapeutic agent if an integral sum for six deconvoluted Gaussian function energy band profiles (from 1000 $cm^{-1}$ to 1140 $cm^{-1}$) of greater than or equal to 14.8 is detected.

In some embodiments, the range of preselected frequencies is from 1600 $cm^{-1}$ to 1700 $cm^{-1}$. In some embodiments, a ratio of integral values the α-helix/β-sheet peaks of less than or equal to 2.1 is an indication of melanoma in the subject. In some embodiments, a ratio of integral values the α-helix/β-sheet peaks of less than or equal to 2.1 is an indication of non-Hodgkin's lymphoma in the subject.

In some embodiments, a ratio of integral values the α-helix/β-sheet peaks of less than or equal to about 2.1 is an indication of melanoma in the subject. In some embodiments, a ratio of integral values the α-helix/β-sheet peaks of less than or equal to about 2.1 is an indication of non-Hodgkin's lymphoma in the subject.

In some embodiments, the range of preselected frequencies is from 1000 $cm^{-1}$ to 1140 $cm^{-1}$. In some embodiments, an integral sum of greater than 14.8 is an indication of melanoma in the subject. In some embodiments, an integral sum of greater than 14.8 is an indication of non-Hodgkin's lymphoma in in the subject.

In some embodiments, the range of preselected frequencies is from 1000 $cm^{-1}$ to 1140 $cm^{-1}$. In some embodiments, an integral sum of greater than about 14.8 is an indication of melanoma in the subject. In some embodiments, an integral sum of greater than about 14.8 is an indication of non-Hodgkin's lymphoma in in the subject.

In one aspect, disclosed herein is a method for detecting melanoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of melanoma;
wherein:
a peak at 1638-1644 $cm^{-1}$ is an indication of melanoma in the subject; or
a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is an indication of melanoma in the subject; or
an integral sum for six deconvoluted Gaussian function energy profiles (from 1000 $cm^{-1}$ to 1140 $cm^{-1}$) of greater than or equal to 14.8 is an indication of melanoma in the subject.

Figure 5:
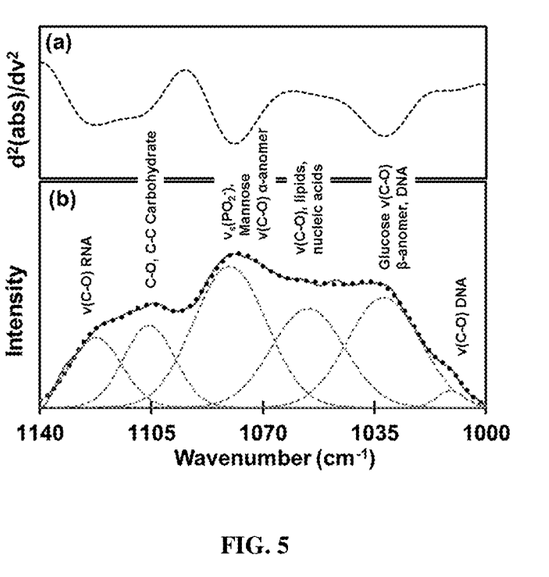
FIG. 5. Analysis of carbohydrates and nucleic acids. (a) The representative of the second derivatives of the ATR-FTIR absorbance spectra confined to 1140-1000 $cm^{-1}$. (b) Deconvolution of spectral range into six Gaussian band profiles by approximating number and position using minima of second derivatives.

Furthermore, to quantify tumor-associated alteration within this complex spectral region of 1140-1000 $cm^{-1}$, deconvolution of experimental spectra into Gaussian function band profiles is further employed. Six Gaussian function energy band profiles (FIG. 5(b)) are used to fit the spectra by approximating number and position using the minima of second derivatives (FIG. 5(a)). The sum of the integral areas covered by six bands (integral values) is then statistically analyzed to evaluate the tumor-associated alteration in the serum.

In one aspect, disclosed herein is a method for detecting non-Hodgkin's lymphoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of non-Hodgkin's lymphoma;
wherein:
a peak at 1636-1642 $cm^{-1}$ is an indication of non-Hodgkin's lymphoma in the subject; or
a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is an indication of non-Hodgkin's lymphoma in the subject; or
an integral sum for six deconvoluted Gaussian function energy band profiles (from 1000 $cm^{-1}$ to 1140 $cm^{-1}$) of greater than or equal to 14.8 is an indication of non-Hodgkin's lymphoma in the subject.

In some embodiments, the sample is a tissue sample, skin sample, blood sample, serum sample, or plasma sample. In some embodiments, the method further comprises Fourier transformation of the absorbance spectrum.

In some aspects, disclosed herein is a method for treating melanoma, comprising:
detecting melanoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of melanoma; and
administering a chemotherapeutic agent if:
i) a peak is detected at 1638-1644 $cm^{-1}$; and/or
ii) a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is detected; and/or
iii) an integral sum for six deconvoluted Gaussian function energy band profiles (from 1000 $cm^{-1}$ to 1140 $cm^{-1}$) of greater than or equal to 14.8 is detected.

In some aspects, disclosed herein is a method for treating non-Hodgkin's lymphoma, comprising:
detecting non-Hodgkin's lymphoma, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of non-Hodgkin's lymphoma; and
administering a chemotherapeutic agent if:
i) a peak is detected at 1636-1642 $cm^{-1}$; and/or
ii) a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is detected; and/or iii) an integral sum for six deconvoluted Gaussian function energy band profiles (from 1000 $cm^{-1}$ to 1140 $cm^{-1}$) of greater than or equal to 14.8 is detected.

In some embodiments, the IRE comprises a diamond crystal, a germanium crystal, or a zinc selenide crystal. In some embodiments, the IRE comprises a diamond crystal.

In some embodiments, the absorption spectrum is recorded over a range of preselected frequencies. In some embodiments, the range of preselected frequencies is from 50 $cm^{-1}$ to 3700 $cm^{-1}$. In some embodiments, a peak at 1636-1642 $cm^{-1}$ is an indication of non-Hodgkin's lymphoma in the subject. In some embodiments, the method further comprises administering a chemotherapeutic agent if a peak is detected at 1636-1642 $cm^{-1}$.

In some embodiments, a ratio of integral values of Gaussian function energy profiles representing $\alpha$-helix (about 1652 $cm^{-1}$) and $\beta$-sheet (about 1630 $cm^{-1}$) protein secondary structures (as obtained from the deconvolution of amide I, 1600-1700 $cm^{-1}$) of less than or equal to 2.1 is an indication of non-Hodgkin's lymphoma in the subject. In some embodiments, the method further comprises administering a chemotherapeutic agent if a ratio of integral values of Gaussian function energy profiles representing $\alpha$-helix (about 1652 $cm^{-1}$) and $\beta$-sheet (about 1630 $cm^{-1}$) protein secondary structures (as obtained from the deconvolution of amide I, 1600-1700 $cm^{-1}$) of less than or equal to 2.1 is detected.

In some embodiments, an integral sum for six deconvoluted Gaussian function energy band profiles (from 1000 $cm^{-1}$ to 1140 $cm^{-1}$) of greater than or equal to 14.8 is an indication of non-Hodgkin's lymphoma in the subject. In some embodiments, the method further comprises administering a chemotherapeutic agent if an integral sum for six deconvoluted Gaussian function energy band profiles (from 1000 $cm^{-1}$ to 1140 $cm^{-1}$) of greater than or equal to 14.8 is detected.

In some embodiments, a peak at about 1640 $cm^{-1}$ is an indication of melanoma in the subject. In some embodiments, a peak at about 1638 $cm^{-1}$ is an indication of non-Hodgkin's lymphoma in the subject. In some embodiments, the method further comprises administering a chemotherapeutic agent if a peak is detected at about 1638 $cm^{-1}$ or about 1640 $cm^{-1}$.

In some embodiments, the sample is a tissue sample, skin sample, blood sample, serum sample, or plasma sample. In some embodiments, the method further comprises Fourier transformation of the absorbance spectrum.

In one aspect, disclosed herein is a method for detecting a cancer, comprising:
depositing a sample comprising a plurality of cells on an internal reflection element (IRE);
directing a beam of infrared (IR) radiation through the IRE under conditions such that the IR radiation interacts with the plurality of cells;
recording an absorption spectrum; and
comparing the absorption spectrum to a control spectrum to detect the presence of a cancer;
wherein a difference in absorbance at one or more frequencies compared to the control spectrum is an indication of cancer in the sample.

In some embodiments, the absorption spectrum is recorded over a range of preselected frequencies. In some embodiments, the range of preselected frequencies is from 1000 $cm^{-1}$ to 1140 $cm^{-1}$. In some embodiments, the range of preselected frequencies is from 1190 $cm^{-1}$ to 1240 $cm^{-1}$. In some embodiments, the range of preselected frequencies is from 1325 $cm^{-1}$ to 1380 $cm^{-1}$. In some embodiments, the range of preselected frequencies is from 1480 $cm^{-1}$ to 1580 $cm^{-1}$. In some embodiments, the range of preselected frequencies is from 1600 $cm^{-1}$ to 1700 $cm^{-1}$. In some embodiments, the absorption spectrum is subjected to dendrogram tree diagram analysis using Ward's algorithm and squared Euclidian distance measurements, allowing visualization of overall grouping structure, including sub-groups. This provides a distinct clustering in the cancer spectra showing the higher degree of heterogeneity between spectra of cancerous groups. In some embodiments, deconvolution of experimental spectra into Gaussian function band profiles is further employed.

Chemotherapeutic Agents

In some embodiments, the chemotherapeutic agent is selected from treatments for melanoma. Chemotherapeutic agents for the treatment of melanoma include, for example, Aldesleukin, Cobimetinib, Cotellic (Cobimetinib), Dabrafenib, Dacarbazine, IL-2 (Aldesleukin), Imlygic (Talimogene Laherparepvec), Interleukin-2 (Aldesleukin), Intron A (Recombinant Interferon Alfa-2b), Ipilimumab, Keytruda (Pembrolizumab), Mekinist (Trametinib), Nivolumab, Opdivo (Nivolumab), Peginterferon Alfa-2b, PEG-Intron (Peginterferon Alfa-2b), Pembrolizumab, Proleukin (Aldesleukin), Recombinant Interferon Alfa-2b, Sylatron (Peginterferon Alfa-2b), Tafinlar (Dabrafenib), Talimogene Laherparepvec, Trametinib, Vemurafenib, Yervoy (Ipilimumab), and Zelboraf (Vemurafenib).

In some embodiments, the chemotherapeutic agent is selected from treatments for non-Hodgkin's lymphoma. Chemotherapeutic agents for the treatment of non-Hodgkin's lymphoma include, for example, Acalabrutinib, Adcetris (Brentuximab Vedotin), Aliqopa (Copanlisib Hydrochloride), Arranon (Nelarabine), Axicabtagene Ciloleucel, Beleodaq (Belinostat), Belinostat, Bendamustine Hydrochloride, Bendeka (Bendamustine Hydrochloride), BiCNU (Carmustine), Bleomycin, Bortezomib, Brentuximab Vedotin, Calquence (Acalabrutinib), Carmustine, Chlorambucil, Copanlisib Hydrochloride, Hydroxydaunorubicin, Cyclophosphamide, Cytarabine Liposome, Denileukin Diftitox, DepoCyt (Cytarabine Liposome), Dexamethasone, Doxorubicin Hydrochloride, Folotyn (Pralatrexate), Gazyva (Obinutuzumab), Ibritumomab Tiuxetan, Ibrutinib, Idelalisib, Imbruvica (Ibrutinib), Intron A (Recombinant Interferon Alfa-2b), Istodax (Romidepsin), Lenalidomide, Leukeran (Chlorambucil), Mechlorethamine Hydrochloride, Methotrexate, Mozobil (Plerixafor), Mustargen (Mechlorethamine Hydrochloride), Nelarabine, Obinutuzumab, Oncovin, Ontak (Denileukin Diftitox), Plerixafor, Pralatrexate, Prednisone, Prednisone (CHIP) chemotherapy regimen, Recombinant Interferon Alfa-2b, Revlimid (Lenalidomide), Rituxan (Rituximab), Rituxan Hycela (Rituximab and Hyaluronidase Human), Rituximab, Rituximab and Hyaluronidase Human, Romidepsin, Treanda (Bendamustine Hydrochloride), Trexall (Methotrexate), Velcade (Bortezomib), Vinblastine Sulfate, Vincristine Sulfate, Vorinostat, Yescarta (Axicabtagene Ciloleucel), and Zevalin (Ibritumomab Tiuxetan).

In some embodiments, for treatment of melanoma, the chemotherapeutic agent is an IL-2 chemotherapeutic agent (Bian, Z., et al.,"Cd47-Sirp$\alpha$ interaction and IL-10 constrain inflammation-induced macrophage phagocytosis of healthy self-cells," *Proceedings of the National Academy of Sciences*, vol. 113, pp. E5434-E5443, 2016). In some embodiments, unique spectral markers for this deadly form of skin cancer condition can be further confirmed by the use of therapeutics such as Aldesleukin (Amaria, R. N., et al., "Update on use of aldesleukin for treatment of high-risk metastatic melanoma," *ImmunoTargets and therapy*, vol. 4, p. 79, 2015) and Dacarbazine (Ugurel, S., et al., "Dacarbazine in melanoma: from a chemotherapeutic drug to an immunomodulating agent," *Journal of Investigative Dermatology*, vol. 133, pp. 289-292, 2013). In some embodiments, the chemotherapeutic agent is Aldesleukin. In some embodiments, the chemotherapeutic agent is Dacarbazine.

In some embodiments, for treatment of Non-Hodgkin's Lymphoma, the chemotherapeutic agent can be, for example, Cyclophosphamide, Hydroxydaunorubicin, Oncovin, Prednisone (CHIP) chemotherapy regimen (Fisher, R. I., et al., "Comparison of a standard regimen (CHOP) with three intensive chemotherapy regimens for advanced non-Hodgkin's lymphoma," *New England Journal of Medicine*, vol. 328, pp. 1002-1006, 1993). In some embodiments, the chemotherapeutic agent is Cyclophosphamide. In some embodiments, the chemotherapeutic agent is Hydroxydaunorubicin. In some embodiments, the chemotherapeutic agent is Oncovin. In some embodiments, the chemotherapeutic agent is Prednisone (CHIP) chemotherapy regimen.

In some embodiments, in addition to the above listed chemotherapeutic agents, an additional chemotherapeutic agent can also be administered to a subject. Additional chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antis, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional chemotherapeutic agents or therapeutic agents that can be administered in combination with the compounds disclosed herein can also include bevacizumab, sutinib, sorafenib, 2-methoxyestradiol, finasunate, vatalanib, vandetanib, aflibercept, volociximab, etaracizumab, cilengitide, erlotinib, cetuximab, panitumumab, gefitinib, trastuzumab, atacicept, rituximab, alemtuzumab, aldesleukine, atlizumab, tocilizumab, temsirolimus, everolimus, lucatumumab, dacetuzumab, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, oblimersen, plitidepsin, talmapimod, enzastaurin, tipifarnib, perifosine, imatinib, dasatinib, lenalidomide, thalidomide, simvastatin, and celecoxib.

ATR-FTR Spectroscopy

Disclosed herein are novel non-invasive methods for detection of melanoma or lymphoma using a conventional method [attenuated total reflection Fourier transform infrared (ATR-FTIR) spectroscopy] in unconventional ways in order to assess biochemical changes induced by cancer. These novel non-invasive methods allow for individualized route maps for rapid evaluation of cancer status (for example, lymphoma and melanoma) and administration of therapeutic treatments.

The disclosed methods involve the use of an infrared spectrum measuring apparatus. In some embodiments, the apparatus comprises: an internal reflecting element (IRE) comprising a reflection face located on the IRE at a region of intended contact between the IRE and a sample; an infrared radiation source for supplying an evanescent wave of infrared radiation and directing the same from the outside of the IRE to the inside thereof so as to cause the infrared radiation to be incident on the reflection face; and a detector for detecting the once-reflected infrared radiation. Representative, but non-limiting examples of instruments that can provide the infrared radiation source include Fourier Transform Infrared Spectroscopy (FTIR) spectrometers.

A range of preselected frequencies for recording absorbance can be selected based on the cell interactions of interest. In general, the preselected frequencies will range between 50 $cm^{-1}$ and 3700 $cm^{-1}$, in particular between 1000 $cm^{-1}$ and 2000 $cm^{-1}$, or more particular between 1600 $cm^{-1}$ and 1700 $cm^{-1}$. US Patent Publication US2016/0305877 and Applied Spectroscopy Reviews (2008) 43(2):134-179 provide a detailed account of spectral frequencies of the biological tissues, which are hereby incorporated by reference in their entirety.

The term "internal reflection element" or IRE refers to a crystal, prism, or other structure that will admit incoming radiation and reflect the radiation at least once from a surface on the interior of the element, preferably following interaction of the radiation with a sample in contact with the reflecting surface. Following such a reflectance, the radiation can be re-reflected or emitted from the element. Preferably the IRE comprises a diamond crystal, germanium crystal, a zinc selenide crystal, or other material with higher index of refraction than the refractive index of the sample being read that are capable of transmitting IR or visible light.

The term "multi-pass ATR" refers to an attenuated total reflectance technique in which radiation that is incident on an internal reflectance element having two or more reflection faces within the IRE experiences two or more interactions with a reflection face before exiting the IRE. At these interfaces, the light is totally reflected back into the IRE material. Such interactions are typically referred to as "bounces" or "passes". Application of multi-pass ATR generates a multi-pass ATR spectrum. Typically, the IRE is in contact with a sample, the incident radiation is IR radiation and the exiting radiation subsequently interacts with a detector.

The term "single-pass ATR" refers to an attenuated total reflectance technique in which radiation incident on an internal reflectance element (IRE) having one or more reflection faces within the IRE experiences only one interaction with a reflection face before exiting the IRE. At this interface, the light is totally reflected back into the IRE material. Application of single-pass ATR generates a single-pass ATR spectrum.

The term "reflecting surface" refers to a surface capable of reflecting incident radiation. On the IR surface where the sample is deposited, the incident light is at an angle greater than the critical angle and hence experiences total internal reflection. There is no transmission of light at this interface, but rather an evanescent wave that escapes out of the surface of the IRE but is coupled back into the IRE material. Indeed, the technique of attenuated total internal reflection (ATR) is based on the principle that an evanescent wave interacts with a sample that is within one fifth of one wavelength of the dielectric boundary.

Attenuated total reflection (ATR) spectroscopy is predicated on the concept that, when light traveling within a medium impinges upon an interface between that medium and a medium of lower refractive index, it either passes into the second medium or is totally internally reflected, depending on whether the quantity $[n_1/n_2 \sin \theta_i]$ is less than or greater than one. In this relationship, $n_1$ and $n_2$ are the refractive indices of the first and second media, respectively, and $\theta_i$ is the angle of incidence. If $n_1/n_2 \sin \theta_i$ is greater than one, total internal reflection occurs. Although the internal reflection is referred to as total, the light, during the reflection process, penetrates a short distance into the second medium. The depth of penetration depends in a predictable fashion on the refractive indices of the two media and the angle of incidence, and is typically on the order of tenths of the wavelength of the light. If the incident light includes a wavelength absorbed by a constituent of the second medium, light of such wavelength will be partially absorbed or attenuated during reflection due to the penetration of the light into the second medium. This effect is referred to as attenuated total reflection. Due to the very shallow penetration of the light into the second medium, ATR is a useful technique for measuring absorbance by strongly absorbing materials. ATR has also been particularly useful for measuring absorbance of material deposited on a surface. Attenuated total reflection spectroscopy is widely used to collect an absorption spectrum from samples that are too opaque for direct absorption measurements.

In practice, one surface of an internal reflecting element (IRE) is placed in contact with a test sample. An incident beam of radiation is directed through the IRE so that it is totally internally reflected at the boundary between the IRE and the test sample. Some of the energy of the incident radiation is absorbed by the test sample through evanescent coupling. The amount of absorption is representative of the molecular structure and/or the molecular species found in the test sample. The reflected radiation, therefore, includes information from which an absorption spectrum for the test sample can be acquired. IREs utilizing total internal reflection or attenuated total reflection principles are commonly found in optical systems designed to analyze samples by assessing the optical constants of the sample and by establishing the physical and chemical composition thereof. Examples of IREs disposed in various optical systems are shown, for example, in U.S. Pat. Nos. 4,602,869 and 3,393,603. In some embodiments, the IRE is a germanium crystal or a zinc selenide crystal. The angle of incidence is defined as the angle between the ray direction and the normal to the surface. A 45-degree angle of incidence is often convenient for a multi-pass FTIR-ATR element. However, the angle of incidence and the composition of an element can be varied to optimize the parameters for a given experiment.

Mathematical and statistical operations that are performed in the course of practicing the present methods can be performed using any suitable computational equipment and software. For example, a commercially available personal computer can be used as a platform for software that can facilitate the acquisition of data, the calculation of difference spectra and perform spectral and other analysis. Computers networked with an FTIR instrument can be employed to acquire data on one machine and process it on another. Suitable data acquisition and management software packages can be designed and written de novo or can be purchased. Suitable commercially available software packages can include SCANTRAQ BASIC™ software package available from FTG Software Associates of Princeton, N.J., and GRAMS/32™ Version 5.2 software package, available from ThermoGalactic of Salem, N.H.

In some embodiments, the process of acquiring a spectrum of a sample is automated. Suitable commercially available software packages for automated spectrum acquisition include the WINFIRST™ package available from Thermo Mattson of Madison, Wis., and the AUTOPRO™ software package available from Pike Technologies, Inc. of Madison, Wis. These software packages can be employed to automate spectrum acquisition and can be useful for analyzing large numbers of samples. In some embodiments, the process is fully automated and can comprise an autosampler to inject and remove samples and a spectrum acquisition software package to run an FTIR microscope or FTIR bench accessory. Additionally, the identified software packages can be modified, or software can be written or purchased, to perform the various mathematical and statistical operations that can be performed when acquiring data by employing the present inventive methods. For example, software can be provided and employed to analyze an acquired spectrum, whereby the water component is automatically subtracted from the spectrum and the quality and quantity of secondary structure is subsequently identified using algorithms referred to, incorporated and disclosed herein. In this embodiment, a researcher can simply prepare the autosampler, configure the software and begin the process.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "sample" or "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

A number of embodiments of the invention have been described. Nevertheless, it will be understood that various modifications may be made without departing from the spirit and scope of the invention. Accordingly, other embodiments are within the scope of the following claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

ATR-FTIR Spectral Discrimination Between Normal and Tumorous Mouse Models of Lymphoma and Melanoma from Serum Samples This example presents attenuated total reflection Fourier transform infrared (ATR-FTIR) spectroscopy of dried serum samples to assess biochemical changes induced by non-Hodgkin's lymphoma and subcutaneous melanoma. An EL4 mouse model of non-Hodgkin's lymphoma and a B16 mouse model of subcutaneous melanoma are used to extract a snapshot of tumor-associated alteration in the serum. The study of both cancer-bearing mouse models in wild types and their corresponding control types, emphasizes the diagnostic use for non-Hodgkin's lymphoma and melanoma skin cancer. Infrared absorbance values of the different spectral bands, hierarchical clustering and integral values of the component bands by curve fitting, show statistically significant differences (student's t-test, two-tailed unequal variance p-value <0.05) between spectra representing healthy and tumorous mouse. This technique is useful for having individualized route maps for rapid evaluation of cancer status (for example, lymphoma and melanoma) and associated therapeutic modalities.

Background

The incidence rates of cutaneous melanoma[1], a deadly form of skin cancer, has been increasing in many regions and populations over the last few decades. The increase has been of the order of 3-7% per year among fair-skinned populations[3]. At the same time, non-Hodgkin's lymphoma (NHL)[4], a solid tumorous condition of the immune system with a wide range of histological appearance and clinical features, accounts for 4.3% of all new cancer cases in the US[5]. Although significant improvement has been made to stabilize the number of NHL cases and to increase its five-year survival rate, the existing diagnostic techniques, which include histological examination using biopsy, are time-consuming, invasive, costly, and are not accessible to the entire at-risk population. Developing a rapid and reliable prescreening strategy for melanoma and lymphoma is thus critical because the early diagnosis and treatment of these malignancies improves[6,7] the patient's chances of survival.

Fourier Transform Infrared (FTIR) spectroscopy is an attractive technique for a rapid, reliable and affordable screening of multiple diseases[8-11]. This technique extracts a snapshot of molecular components within the diagnostic medium and provides a holistic biochemistry of that medium[12]. The FTIR spectroscopy combined with appropriate data handling frameworks has been applied in oncological studies[9] such as studies involving the cancers of the cervix[13], the lung[14], the breast[15], the skin[16], the gastro-intestine[17], the prostate[18], the colon[19], the ovary[20], the urinary bladder[21] and many other body parts. These studies have reported that the molecular structural rearrangement associated with cancer development alters the vibrational mode of the molecular functional groups of the affected tissues as manifested in spectral markers or signatures. Furthermore, the Attenuated Total Reflection (ATR) sampling mode[22] of FTIR spectroscopy represents a complementary approach for the clinical application[10,23], compared to other infrared approaches[24]. In this mode, high-quality results with better spectral reproducibility compared to other modes can be obtained by the use of fluid samples[25]. It has been noted that metabolic discharges into the body fluids (saliva, excreta, blood and other tissue fluids) from the proximate cancerous tissue change the constituent molecules, providing strong guidance for subsequent clinical assessment[21,26]. ATR-FTIR spectroscopy of body fluids has thus attracted much attention in the scientific community including clinicians for rapid detection of various health conditions[27]. In this example, the diagnostic capability of ATR-FTIR spectroscopy is shown for melanoma and non-Hodgkin's lymphoma.

Results

Figure 1:
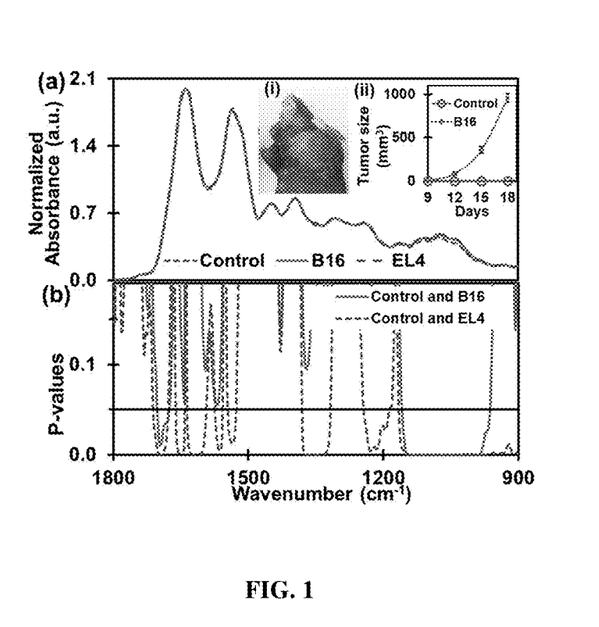

Discrimination of absorbance values. FIG. 1(a) shows the average normalized ATR-FTIR spectrum of air dried serum samples extracted from tumor-bearing mouse models of EL4 lymphoma (n=8) and B16 melanoma (n=8) in wild types and corresponding control types (n=15). Using the student's t-test, p-values (two-tailed unequal variance), the most discriminatory features of the spectrum within the spectral range 1800-900 $cm^{-1}$, were extracted (FIG. 1(b)). Interestingly, the features observed for different groups enable the classification between control cases and malignant cases and between the two malignant cases of lymphoma and melanoma. Molecular assignments[26,28-32] of five spectral bands showing discrimination of EL4 lymphoma from their control types, with higher significance (i.e. p-values <0.05) are presented in Table 1. These are the bands originating from (i) amide I of protein, (ii) amide II of protein (iii) C—H deformation of $CH_3/CH_2$ groups, (iv) asymmetric phosphate I, and (v) carbohydrates and nucleic acids. Similarly, two spectral bands showing the significant difference between B16 melanoma and their control types are also shown in the regions i and v of the table. Significant alteration in the amide I band and the complex band of carbohydrate and the nucleic acids are observed for B16 melanoma. The difference in the p-values observed between lymphoma and melanoma could be attributed to the difference in mechanism of each type of tumor development, while similarity could be attributed to common etiology[33].

TABLE 1

Discriminatory infrared spectral bands of dried serum with biomolecular assignments

| | Wavenumber region (cm$^{-1}$) | Assignments |
|---|---|---|
| i | 1700-1600 | Amide I of proteins: (α-helical, β-pleated sheet, β-turns, random coils and side-chain structures), ν(C═O), ν(C—N), CNN. |
| ii | 1480-1580 | Amide II of proteins: (α-helical, β-pleated sheet, unordered conformation structures), δ(N—H), ν(C—N). |
| iii | 1325-1380 | C—H deformation: due to CH$_3$/CH$_2$ bending (groups in α and β anomers) of lipids and proteins. |
| iv | 1190-1240 | Asymmetric phosphate I: $\nu_{as}(PO_2^-)$ of lipid phosphates. |
| v | 1000-1140 | Carbohydrates and nucleic acids: C—O, C—C stretch, C—H bend, deoxyribose/ribose DNA, RNA, $\nu_s(PO_2^-)$. |

Figure 2:
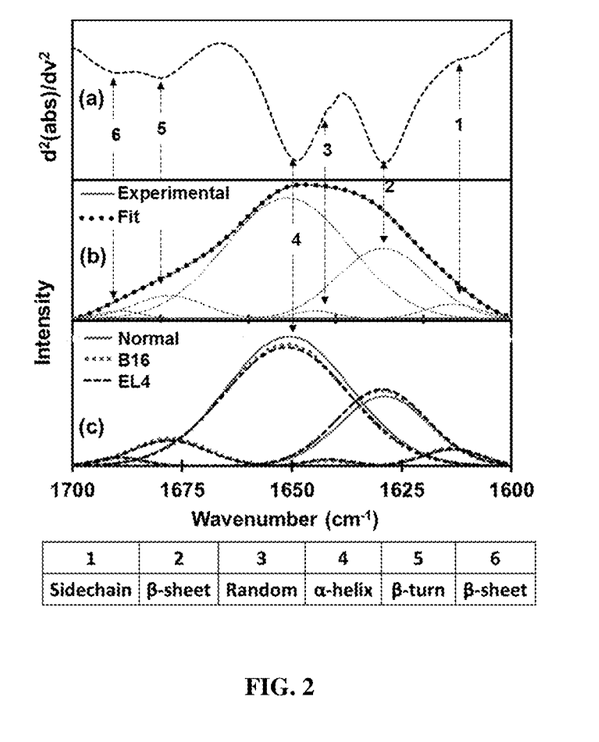

Protein secondary structures analysis by deconvolution of amide I band. Amide I band region with strong absorption is highly sensitive to the minor changes in molecular geometry and hydrogen bonding patterns of protein molecules. This sensitive vibrational band of protein backbone relates to protein secondary structural components and gives rise to different C═O stretching frequency for each structure[34]. Studies have shown that the secondary structure information obtained from the spectral deconvolution (or fitting)[34,35] of the amide I band are in agreement with information from X-ray crystallographic structures of proteins[36-38]. Secondary structure analysis is done by the deconvolution of the experimental amide I band into component energy bands[39]. The minima of second derivatives of spectra (FIG. 2(a)) were used to approximate the position and number of Gaussian function energy profiles required to fit an experimental curve. Once the positions were determined, six Gaussian profile bands were used by minimizing Root Mean Square (RMS) error via a Levenberg-Marquardt function such that the simulated curve best fits the experimental curve as shown in FIG. 2(b). Energy bands at approximately 1652 and 1630 (in cm$^{-1}$) have been assigned[40,41] as vibrational modes of α-helix and β-sheet structural components respectively. The α-helix component integral value (area under the Gaussian band) decreases while the β-sheet component integral value increases simultaneously due to tumorigenesis (FIG. 2(c)). However, the integrals of component bands side-chain (~1610 cm$^{-1}$), random coils (~1645 cm$^{-1}$), β-turn (~1682 cm$^{-1}$) and β-sheet with opposite alignments[40] (1690 cm$^{-1}$) do not show any appreciable change due to the tumor development.

Figure 3:
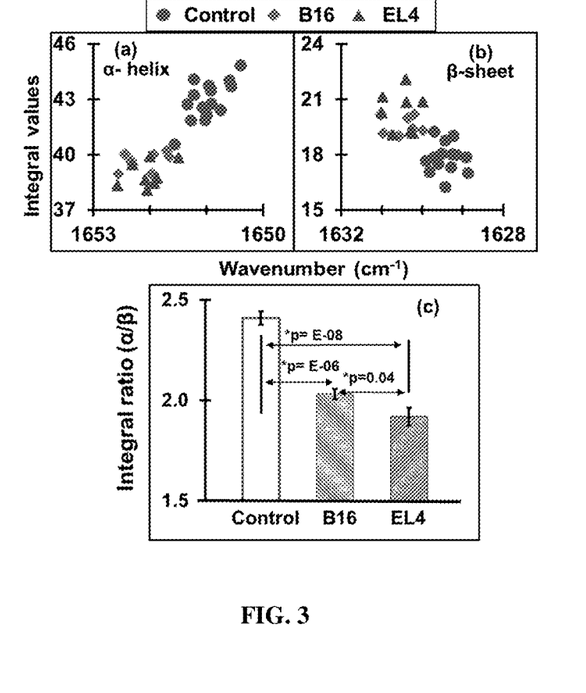
FIG. 3. Plots of the protein secondary structures (α-helix, β-sheet) and their ratio. (a) Quantified integral (area covered) values of α-helix components are less for tumorous cases compared to control. (b) Integral values of β-sheet components are higher for tumorous cases compared to control (c) Bar graph representation of average integral ratios between α-helix and β-sheet for control, B16 and EL4. Significant alteration in integral ratio (α-helix/β-sheet) is found between control and tumorigenic case.

In order to demonstrate alterations in structural components due to malignancy, integral values of α-helical and β-sheet structures and their ratios were statistically analyzed. FIGS. 3(a) and 3(b) show the cluster plots of the integrals of α-helical and β-sheet structures respectively for the control, B16 and EL4 mice. These figures clearly demonstrate a separation between the corresponding integral values for the control and tumorous groups for β-sheet and α-helix. Furthermore, the ratio of integral values α-helix to β-sheet (FIG. 3(d)) is always less than the control values for both mouse models with greater than 99% significance.

Amide I and II absorbance values. Amide I and Amide II are the two major bands of the infrared spectrum for protein interrogation in biological materials[28,29]. The intensity and position of these bands, determined by backbone confirmation of the hydrogen bonding pattern change with malignancies[13,42]. Amide I band position shifts towards the lower wavenumber due to malignancy. The average position of amide I representing control is at 1641 cm$^{-1}$, B16 is 1640 $^{-1}$ and that of EL4 is 1638 cm$^{-1}$, but the position of amide II is exactly at 1538 cm$^{-1}$ for all three types. Altered position of amide I is statistically significant for EL4 (*p=0.001) while that of B16 is not significant (*p=0.2). Similarly, an altered ratio between amide I and amide II absorbance values is significant (*p=0.01) for EL4 lymphoma but not (*p=0.3) for B16 melanoma in comparison to the control groups.

Nucleic acids and carbohydrate analysis. In the region 1140-1000 cm$^{-1}$, there are plenty of overlapping vibrational modes of biological macromolecules[9] with the major contribution of nucleic acids and carbohydrates[12]. Bands approximately at 1121 cm$^{-1}$ arise from RNA absorbance, whereas the band at 1020 cm$^1$ arises from DNA absorbance[43]. The spectral band near 1080 cm$^{-1}$ is due to $\nu_s(PO_2^-)$, and the band approximately at 1056 cm$^{-1}$ corresponding to the $\nu_s(PO_2^-)$ absorbance of phosphodiesters of nucleic acids and the O—H stretching coupled with C—O bending of C—OH groups of carbohydrates[44]. Similarly, absorbance near 1033 cm$^{-1}$ and 1076 cm$^1$ are due to the presence of glucose (C—O stretching carbohydrate, β-anomer) and mannose (C—O stretching carbohydrate α-anomer)[10]. Alteration in concentration of two sequences of basic genetic materials—(a) RNA (which play an active role in protein synthesis) and (b) DNA (which is primarily involved in the storage, copying and transferring genetic information), has been already reported from the tissue analysis of NHL[43] and subcutaneous melanoma[45]. Due to the fluctuation in these biomolecules, there is a dissimilarity between malignant groups from their control types. In order to verify these dissimilarities, Hierarchical Cluster Analysis (HCA) was used along with spectral deconvolution within this spectral range.

Figure 4:
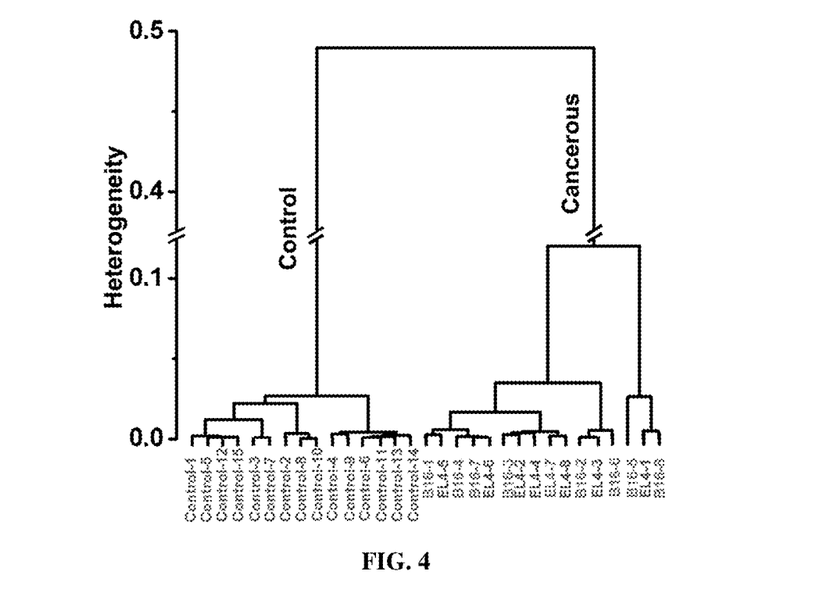
FIG. 4. Dendrogram of hierarchical cluster analysis. Dendrogram tree diagram performed within spectral range 1140-1000 $cm^{-1}$, by using Ward's algorithm and squared Euclidian distance measurements. The spectra are correctly classified. Control spectra appear grouped together, which describes a high degree of similarity within the groups. Similarly, there is a distinct clustering in the cancer spectra in two subgroups showing the higher degree of heterogeneity between cancerous spectra.

HCA is commonly employed to identify the similarities between the FTIR spectra by using the distances between spectra and aggregation algorithms[14]. The dendrogram of HCA is performed with ATR-FTIR spectra of control, B16, and EL4 mice, are shown in FIG. 4. Dendrogram tree diagram performed using spectral region of nucleic acids and carbohydrates, 1140-1000 cm$^1$, using Ward's algorithm and squared Euclidian distance measurements, allow us to visualize of overall grouping structure, including the subgroups. The distinct cluster for the control spectra which are grouped together, describing a high degree of similarity within the groups. Similarly, there is a distinct clustering in the cancer spectra showing the higher degree of heterogeneity between spectra of cancerous groups.

Figure 6:
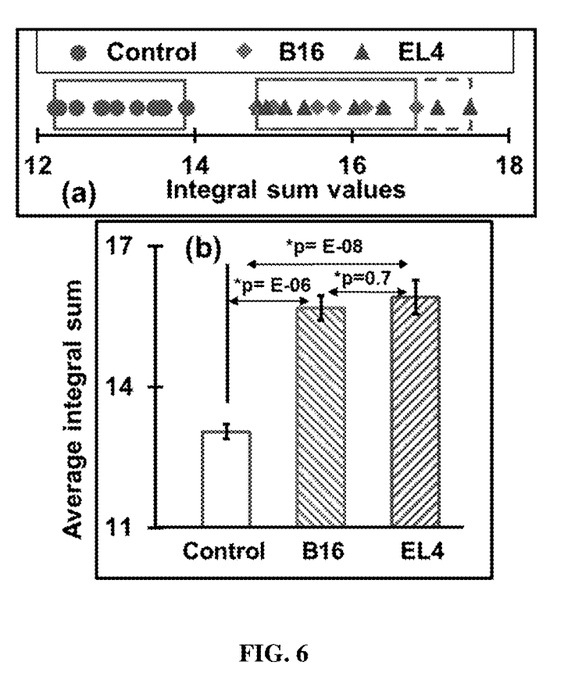
FIG. 6. The integral sum of Gaussian energy profiles used to fit experimental curve within 1000-1140 $cm^{-1}$. (a) The calibration curve obtained after adding integral values of energy profiles used to fit experimental curves. The sum of integral values of control groups cluster within the approximate range 12-14, B16 covers the range 15-17 and EL4 covers 15-18. (b) Bar graph representation of average value of integral sum which shows significant difference between control and tumorigenic case.

Furthermore, to quantify tumor-associated alteration within this complex spectral region of 1140-1000 cm$^{-1}$, deconvolution of experimental spectra into Gaussian function band profiles is further employed. Six Gaussian function energy band profiles (FIG. 5(b)) are used to fit the spectra by approximating number and position using the minima of second derivatives (FIG. 5(a)). The sum of the integral areas covered by six bands (integral values) is then statistically analyzed to evaluate the tumor-associated alteration in the serum. A calibration curve is obtained, as shown in FIG. 6(a) between control and tumorous groups. A clear separation between control (12-14) and cases of tumorigenicity B16 (15-17) and EL4 (15-18) is found while adding the integral values. Bar graph representation of these values with significance greater than 99% is shown in FIG. 6(b).

Discussion

The results of the present example show remarkable differences (Table 2) between the ATR-FTIR spectra of serum samples representing tumor-bearing mouse models of melanoma (n=8) and NHL (n=8) from their control (n=15) types.

TABLE 2

Quantified values of discriminatory features.

| | Spectral deconvolution | | | | | Absorbance values | |
|---|---|---|---|---|---|---|---|
| | Amide I 1600-1700 cm$^{-1}$ | | Mixed region 1000-1140 | Amide I and II | | $\nu_{as}$ (PO$_2^-$) ~1212 cm$^{-1}$ | C—H def. ~1335 cm$^{-1}$ |
| | Integral values | | Ratio | Integral | Position | Ratio: abs | | |
| Feature | α-helix | β-sheet | (α/β) | sum | amide I | Amide I/II | | |
| Control | 40.6-44.9 | 16.3-19.3 | 2.2-2.7 | 12.2-13.9 | 1640-1645 | 1.10-1.13 | 0.42-0.44 | 0.54-0.59 |
| B16 | 38.9-40.2 | 19-20.2 | 1.9-2.1 | 14.8-16.8 | 1638-1644 | 1.10-1.15 | 0.42-0.45 | 0.54-0.59 |
| EL4 | 38.1-39.9 | 19.1-21.1 | 1.7-2.1 | 14.8-17.1 | 1636-1642 | 1.12-1.15 | 0.43-0.46 | 0.58-0.59 |

Clear separation can be seen between control and cancerous cases (both B16 and EL4) while comparing integral values of α-helix, β-sheet structure components, and their ratios. Similarly, altered position of amide I peak, amide I/amide II ratio and absorbance values at 1212 and 1335 cm$^{-1}$ show significant difference only between EL4 and control.

The differentiating signatures between spectra are obtained by observing (i) p-values comparison, (ii) the spectral position and ratio analysis of amide peaks (iii) the fit of the experimental spectra and (iv) the employment of multivariate analysis (HCA). This difference between control and tumorous cases is evident through the gradual changes in the intensities of the absorption of mainly proteins, carbohydrates and nucleic acids in the serum. It is noted that serological tests show the alterations of certain proteins, peptides, and nucleic acids (DNA, mRNA) for patients with melanoma[46] and lymphoma[47]. Manifestations of these alteration in biomolecules (serological markers) are most likely for the tumor-induced alteration in identifying spectral markers.

Herein, this example shows rapid and reliable spectroscopic discrimination of B16 melanoma and EL4 lymphoma from their control types. The B16 murine tumor model remains an indispensable model for metastasis and therapeutic studies of human melanoma skin cancer[48]. Similarly, development of the EL4 murine tumor model is considered as a huge benefit[49] to the human NHL research cancer. This technology can be used as a personalized diagnostic tool in which patient-to-patient and within a patient over time (due to health conditions or other factors) differences in molecular signatures allows the assessment of disease status and personalized drug management. To be used as a patient-to-patient screening test, a normal range of spectral markers unique to the particular disease is confirmed by using a statistically significant set of normal serum samples. These average normal values are incorporated into the program which identifies the deviations of the test sample from the average values. Technological advancement of ATR-FTIR spectroscopy of serum sample to discriminate normal and tumorous conditions thus can support an increased compliance rate in the eligible population for tumor screening and can also aide the physician's decision for advanced histological examination using biopsy.

Materials and Methods

Mouse tumor models. C57BL/6J mice (6-8 weeks, 20-22 g, the Jackson Laboratory) were engrafted with B16 melanoma or EL4 lymphoblast via subcutaneous (s. c.) route with 2×10$^5$ of each cell line. B16 and EL4 cells were obtained from American Type Cultural Collection (ATCC) and maintained in DMEM with 10% FBS prior to use. Mice were euthanized after 3 weeks of tumor inoculation, when tumors were larger than 1000 mm$^3$ in size (see FIG. 1, inset (i)). Serum samples from tumor-bearing mice and healthy mice were isolated and stored in −80° C. until analysis. All experiments using animals described in this study were approved (protocol number: A17015) by the Institutional Animal Care and Use Committee (IACUC) of Georgia State University, Atlanta, Ga. and experiments were conducted according to the guideline of Office of Laboratory Animal Welfare (OLAW), Assurance number: D16-00527(A3914-01).

Fourier transform infrared spectroscopy. A Bruker Vertex 70 FTIR spectrometer series with KBr beam splitter and Deuterated Tri-Glycine Sulfate (DTGS) pyroelectric detector was used. The spectrometer was fixed with an MVP-Pro ATR accessory from Harrick-Scientific having diamond crystal (1mm×1.5mm) as an internal reflection element and configured to have a single reflection of the infrared radiation. In all measurements, medium Blackman-Harris apodization function was employed with a resolution of 4 cm$^{-1}$ with zero filling factor 4 to provide the best resolving ability with a minimum signal-to-noise ratio. Furthermore, for the optimization of the detector response and for the prevention of its saturation, aperture size is set to 2.5 mm.

Sampling and scanning. ATR crystal was first cleaned using sterile phosphate buffered saline followed by ethanol. A cleanness test was then conducted, where the absorbance spectrum obtained without a sample to ensure it have no signal peaks higher than the environmental noise level. Background measurement was then performed prior to each spectral measurement by scanning a clean diamond crystal surface, and having its value subtracted from the sample signal spectrum. After setting these parameters, serum samples of one microliter volume were deposited on the crystal surface and allowed to air dry (~8 minutes) at room temperature. As the scanning runs, an evanescent wave with an approximate penetration depth of ~2.5 microns (for mid-IR) interacts with the sample. Each sample was scanned multiple times to get eight (or more) high-quality spectral curves, and the last six reads of the 100 co-added scans for each sample (total of 600 scans) were averaged.

Spectral analysis. Using OPUS 7.2 spectroscopy software, all the spectra were internally normalized[12] by scaling within the fingerprint region 1800-900 cm$^{-1}$. In these normalized spectra, the absorbance values of amide I band position (~1642 cm$^{-1}$) is 2 AU (corresponding to ~99% absorption) according to the Beer-Lambert algorithm. The significance of difference in absorbance values between control and diseased cases at different spectral marker positions were then tested by using the student's t-test (two-tailed unequal variance) p-values. The significance test is then followed by the discrimination of protein secondary structures by deconvolution of the spectra into Gaussian function energy bands within the amide I band position 1700-1600 cm$^{-1}$. Using OriginPro 2015 software, Hierarchical Cluster Analysis (HCA) was employed to identify the similarities between the spectra using the range of 1140-1000 cm$^{-1}$. This spectral region has been studied before through the use of tissue biopsy while discriminating lymphoma[43] and melanoma[45] from control groups. Spectral deconvolution within the range was also completed to quantify spectral dissimilarity.

REFERENCES

1 Lens, M. & Dawes, M. Global perspectives of contemporary epidemiological trends of cutaneous malignant melanoma. *British Journal of Dermatology* 150, 179-185 (2004).
2 Siegel, R. L., Miller, K. D. & Jemal, A. Cancer statistics, 2016. *CA: a cancer journal for clinicians* 66, 7-30 (2016).
3 Garbe, C. & Leiter, U. Melanoma epidemiology and trends. *Clinics in dermatology* 27, 3-9 (2009).
4 Fisher, S. G. & Fisher, R. I. The epidemiology of non-Hodgkin's lymphoma. *Oncogene* 23, 6524-6534 (2004).
5 Howlader, N. et al. (2016).
6 Jerant, A. F., Johnson, J. T., Sheridan, C. & Caffrey, T. J. Early detection and treatment of skin cancer. *American family physician* 62, 357-386 (2000).
7 Shipp, M. et al. A predictive model for aggressive non-Hodgkin's lymphoma. *New England Journal of Medicine* 329, 987-994 (1993).
8 Bellisola, G. & Sorio, C. Infrared spectroscopy and microscopy in cancer research and diagnosis. *Am J Cancer Res* 2, 1-21 (2012).
9 Movasaghi, Z., Rehman, S. & ur Rehman, D. I. Fourier transform infrared (FTIR) spectroscopy of biological tissues. *Applied Spectroscopy Reviews* 43, 134-179 (2008).
10 Titus, J., Viennois, E., Merlin, D. & Unil Perera, A. Minimally invasive screening for colitis using attenuated total internal reflectance fourier transform infrared spectroscopy. *Journal of biophotonics* (2016).
11 Titus, J., Ghimire, H., Viennois, E., Merlin, D. & Perera, A. Protein secondary structure analysis of dried blood serum using infrared spectroscopy to identify markers for colitis screening. *Journal of Biophotonics* (2017).
12 Baker, M. J. et al. Using Fourier transform IR spectroscopy to analyze biological materials. *Nature protocols* 9, 1771-1791 (2014).
13 Wood, B. et al. Fourier transform infrared (FTIR) spectral mapping of the cervical transformation zone, and dysplastic squamous epithelium. *Gynecologic oncology* 93, 59-68 (2004).
14 Lewis, P. D. et al. Evaluation of FTIR spectroscopy as a diagnostic tool for lung cancer using sputum. *BMC cancer* 10, 640 (2010).
15 Backhaus, J. et al. Diagnosis of breast cancer with infrared spectroscopy from serum samples. *Vibrational Spectroscopy* 52, 173-177 (2010).
16 Lima, C. A., Goulart, V. P., Côrrea, L., Pereira, T. M. & Zezell, D. M. ATR-FTIR spectroscopy for the assessment of biochemical changes in skin due to cutaneous squamous cell carcinoma. *International journal of molecular sciences* 16, 6621-6630 (2015).
17 Fujioka, N., Morimoto, Y., Arai, T. & Kikuchi, M. Discrimination between normal and malignant human gastric tissues by Fourier transform infrared spectroscopy. *Cancer Detection and Prevention* 28, 32-36 (2004).
18 Gazi, E. et al. Applications of Fourier transform infrared microspectroscopy in studies of benign prostate and prostate cancer. A pilot study. *The Journal of pathology* 201, 99-108 (2003).
19 Rigas, B., Morgello, S., Goldman, I. S. & Wong, P. Human colorectal cancers display abnormal Fourier-transform infrared spectra. *Proceedings of the National Academy of Sciences* 87, 8140-8144 (1990).
20 Theophilou, G., Lima, K. M., Martin-Hirsch, P. L., Stringfellow, H. F. & Martin, F. L. ATR-FTIR spectroscopy coupled with chemometric analysis discriminates normal, borderline and malignant ovarian tissue: classifying subtypes of human cancer. *Analyst* 141, 585-594 (2016).
21 Ollesch, J. et al. It's in your blood: spectral biomarker candidates for urinary bladder cancer from automated FTIR spectroscopy. *Journal of biophotonics* 7, 210-221 (2014).
22 Sommer, A. J., Tisinger, L. G., Marcott, C. & Story, G. M. Attenuated total internal reflection infrared mapping microspectroscopy using an imaging microscope. *Appl. Spectrosc.* 55, 252-256 (2001).
23 Kazarian, S. G. & Chan, K. A. ATR-FTIR spectroscopic imaging: recent advances and applications to biological systems. *Analyst* 138, 1940-1951 (2013).
24 Titus, J., Filfili, C., Hilliard, J. K., Ward, J. A. & Unil Perera, A. Early detection of cell activation events by means of attenuated total reflection Fourier transform infrared spectroscopy. *Applied Physics Letters* 104, 243705 (2014).
25 Chan, K. A. & Kazarian, S. G. Attenuated total reflection Fourier-transform infrared (ATR-FTIR) imaging of tissues and live cells. *Chemical Society Reviews* 45, 1850-1864 (2016).
26 Baker, M. J. et al. Developing and understanding biofluid vibrational spectroscopy: a critical review. *Chemical Society Reviews* 45, 1803-1818 (2016).
27 Orphanou, C.-M. The detection and discrimination of human body fluids using ATR FT-IR spectroscopy. *Forensic science international* 252, e10-e16 (2015).
28 Meurens, M., Wallon, J., Tong, J., Noel, H. & Haot, J. Breast cancer detection by Fourier transform infrared spectrometry. *Vibrational spectroscopy* 10, 341-346 (1996).
29 Gazi, E. et al. A correlation of FTIR spectra derived from prostate cancer biopsies with Gleason grade and tumour stage. *European urology* 50, 750-761 (2006).
30 Gajjar, K. et al. Diagnostic segregation of human brain tumours using Fourier-transform infrared and/or Raman spectroscopy coupled with discriminant analysis. *Analytical Methods* 5, 89-102 (2013).
31 Hands, J. R. et al. Brain tumour differentiation: rapid stratified serum diagnostics via attenuated total reflection Fourier-transform infrared spectroscopy. *Journal of neuro-oncology* 127, 463-472 (2016).
32 Hands, J. R. et al. Attenuated total reflection Fourier transform infrared (ATR-FTIR) spectral discrimination of brain tumour severity from serum samples. *J. Biophotonics* 7, 189-199 (2014).

33 Lens, M. & Newton-Bishop, J. An association between cutaneous melanoma and non-Hodgkin's lymphoma: pooled analysis of published data with a review. *Annals of oncology* 16, 460-465 (2005).

34 Byler, D. M. & Susi, H. Examination of the secondary structure of proteins by deconvolved FTIR spectra. *Biopolymers* 25, 469-487 (1986).

35 Yang, H., Yang, S., Kong, J., Dong, A. & Yu, S. Obtaining information about protein secondary structures in aqueous solution using Fourier transform IR spectroscopy. *Nature protocols* 10, 382-396 (2015).

36 Kong, J. & Yu, S. Fourier transform infrared spectroscopic analysis of protein secondary structures. *Acta biochimica et biophysica Sinica* 39, 549-559 (2007).

37 Surewicz, W. K., Mantsch, H. H. & Chapman, D. Determination of protein secondary structure by Fourier transform infrared spectroscopy: a critical assessment. *Biochemistry* 32, 389-394 (1993).

38 Lu, R. et al. Probing the secondary structure of bovine serum albumin during heat-induced denaturation using mid-infrared fiberoptic sensors. *Analyst* 140, 765-770 (2015).

39 Barth, A. Infrared spectroscopy of proteins. *Biochimica et Biophysica Acta (BBA)-Bioenergetics* 1767, 1073-1101 (2007).

40 Chírgadze, Y. N. & Nevskaya, N. Infrared spectra and resonance interaction of amide-I vibration of the antiparallel-chain pleated sheet. *Biopolymers* 15, 607-625 (1976).

41 Goormaghtigh, E., Cabiaux, V. & Ruysschaert, J.-M. in *Physicochemical methods in the study of biomembranes* 405-450 (Springer, 1994).

42 Hammody, Z., Sahu, R. K., Mordechai, S., Cagnano, E. & Argov, S. Characterization of malignant melanoma using vibrational spectroscopy. *The Scientific World Journal* 5, 173-182 (2005).

43 Andrus, P. G. & Strickland, R. D. Cancer grading by Fourier transform infrared spectroscopy. *Biospectroscopy* 4, 37-46 (1998).

44 Bogomolny, E., Huleihel, M., Suproun, Y., Sahu, R. K. & Mordechai, S. Early spectral changes of cellular malignant transformation using Fourier transform infrared microspectroscopy. *Journal of biomedical optics* 12, 024003-024003-024009 (2007).

45 Mordechai, S. et al. Possible common biomarkers from FTIR microspectroscopy of cervical cancer and melanoma. *Journal of microscopy* 215, 86-91 (2004).

46 Vereecken, P., Cornelis, F., Van Baren, N., Vandersleyen, V. & Baurain, J.-F. A synopsis of serum biomarkers in cutaneous melanoma patients. *Dermatology research and practice* 2012 (2012).

47 Legouffe, E. et al. C-reactive protein serum level is a valuable and simple prognostic marker in non Hodgkin's lymphoma. *Leukemia & lymphoma* 31, 351-357 (1998).

48 Overwijk, W. W. & Restifo, N. P. B16 as a mouse model for human melanoma. *Current Protocols in Immunology*, 20.21. 21-20.21. 29 (2001).

49 Daydé, D. et al. Tumor burden influences exposure and response to rituximab: pharmacokinetic-pharmacodynamic modeling using a syngeneic bioluminescent murine model expressing human CD20. *Blood* 113, 3765-3772 (2009).

50 Jayaweera, P. et al. Uncooled infrared detectors for 3-5 μm and beyond. *Applied Physics Letters* 93, 021105 (2008).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method for detecting melanoma, comprising:
    (a) depositing a sample comprising a plurality of cells on an internal reflection element (IRE);
    (b) directing a beam of infrared (IR) radiation through the IRE under conditions such that the IR radiation interacts with the plurality of cells;
    (c) recording an absorption spectrum; and
    (d) comparing the absorption spectrum to a control spectrum to detect the presence of melanoma;
    wherein a difference in absorbance at one or more frequencies compared to the
    control spectrum is an indication of melanoma in the sample.

2. The method of claim 1, wherein the absorption spectrum is recorded over a range of preselected frequencies.

3. The method of claim 2, wherein the range of preselected frequencies is from 50 $cm^{-1}$ to 3700 $cm^{-1}$.

4. The method of claim 1, wherein a peak at 1638-1644 $cm^{-1}$ is an indication of melanoma in the subject.

5. The method of claim 1, further comprising administering a chemotherapeutic agent when a peak is detected at 1638-1644 $cm^{-1}$.

6. The method of claim 1, wherein a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is an indication of melanoma in the subject.

7. The method of claim 1, further comprising administering a chemotherapeutic agent when a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is detected.

8. The method of claim 1, wherein an integral sum for six deconvoluted Gaussian function energy band profiles (from 1000 $cm^{-1}$ to 1140 $cm^{-1}$) of greater than or equal to 14.8 is an indication of melanoma in the subject.

9. The method of claim 1, further comprising administering a chemotherapeutic agent when an integral sum for six deconvoluted Gaussian function energy band profiles (from 1000 $cm^{-1}$ to 1140 $cm^{-1}$) of greater than or equal to 14.8 is detected.

10. A method for treating melanoma, comprising:
    detecting melanoma using the method of claim 1; and
    administering a chemotherapeutic agent when:
        i) a peak is detected at 1638-1644 $cm^{-1}$; or
        ii) a ratio of integral values of Gaussian function energy profiles representing α-helix (about 1652 $cm^{-1}$) and β-sheet (about 1630 $cm^{-1}$) protein secondary structures (as obtained from the deconvolution of amide I, 1600-1700 $cm^{-1}$) of less than or equal to 2.1 is detected; or iii) an integral sum for six deconvoluted Gaussian function energy band profiles (from 1000 cm$^{-1}$ to 1140 cm$^{-1}$) of greater than or equal to 14.8 is detected.

11. A method for detecting non-Hodgkin's lymphoma, comprising:
    (a) depositing a sample comprising a plurality of cells on an internal reflection element (IRE);
    (b) directing a beam of infrared (IR) radiation through the IRE under conditions such that the IR radiation interacts with the plurality of cells;
    (c) recording an absorption spectrum; and
    (d) comparing the absorption spectrum to a control spectrum to detect the presence of non-Hodgkin's lymphoma;
        wherein a difference in absorbance at one or more frequencies compared to the control spectrum is an indication of non-Hodgkin's lymphoma in the sample.

12. The method of claim 11, wherein the absorption spectrum is recorded over a range of preselected frequencies.

13. The method of claim 12, wherein the range of preselected frequencies is from 50 cm$^{-1}$ to 3700 cm$^{-1}$.

14. The method of claim 11, wherein a peak at 1636-1642 cm$^{-1}$ is an indication of non-Hodgkin's lymphoma in the subject.

15. The method of claim 11, further comprising administering a chemotherapeutic agent when a peak is detected at 1636-1642 cm$^{-1}$.

16. The method of claim 11, wherein a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is an indication of non-Hodgkin's lymphoma in the subject.

17. The method of claim 11, further comprising administering a chemotherapeutic agent when a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is detected.

18. The method of claim 11, wherein an integral sum for six deconvoluted Gaussian function energy band profiles (from 1000 cm$^{-1}$ to 1140 cm$^{-1}$) of greater than or equal to 14.8 is an indication of non-Hodgkin's lymphoma in the subject.

19. The method of claim 11, further comprising administering a chemotherapeutic agent when an integral sum for six deconvoluted Gaussian function energy band profiles (from 1000 cm$^{-1}$ to 1140 cm$^{-1}$) of greater than or equal to 14.8 is detected.

20. A method for treating non-Hodgkin's lymphoma, comprising:
    detecting non-Hodgkin's lymphoma using the method of claim 11; and
    administering a chemotherapeutic agent when:
        i) a peak is detected at 1636-1642 cm$^{-1}$; or
        ii) a ratio of integral values of Gaussian function energy profiles representing α-helix (about 1652 cm$^{-1}$) and β-sheet (about 1630 cm$^{-1}$) protein secondary structures (as obtained from the deconvolution of amide I, 1600-1700 cm$^{-1}$) of less than or equal to 2.1 is detected; or
        iii) an integral sum for six deconvoluted Gaussian function energy band profiles (from 1000 cm$^{-1}$ to 1140 cm$^{-1}$) of greater than or equal to 14.8 is detected.

* * * * *